(12) United States Patent
Niedermann et al.

(10) Patent No.: US 6,307,103 B1
(45) Date of Patent: Oct. 23, 2001

(54) PROCESS FOR THE PREPARATION OF 1,1, 1-TRIFLUORO-2-AMINOALKANES

(75) Inventors: Hans-Peter Niedermann, Bubenheim; Dieter Gutheil, Bad Kreuznach, both of (DE)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/537,910

(22) Filed: Mar. 28, 2000

Related U.S. Application Data

(60) Provisional application No. 60/129,472, filed on Apr. 15, 1999.

(51) Int. Cl.$^7$ .................................................. C07C 209/40
(52) U.S. Cl. ......................... 564/489; 560/172; 562/574
(58) Field of Search ........................... 564/489; 560/172; 562/574

(56) References Cited

U.S. PATENT DOCUMENTS

| | | | |
|---|---|---|---|
| 3,737,462 | * 6/1973 | Cheema et al. | 564/489 |
| 3,959,379 | * 5/1976 | Ottiger | 564/253 |
| 4,840,969 | 6/1989 | Tarnow et al. | 514/617 |
| 5,082,862 | 1/1992 | Tarnow et al. | 514/617 |
| 5,593,996 | 1/1997 | Pees et al. | 514/258 |

FOREIGN PATENT DOCUMENTS

| | | | |
|---|---|---|---|
| 3611193 | 10/1987 | (DE) | C07C/103/76 |
| WO 98/46608 | 10/1998 | (WO) | C07D/487/04 |

OTHER PUBLICATIONS

J.B. Dickey et al., "Fluorinated Aminoanthraquinone Dyes", Ind. Eng. Chem. 48, 1956, 209–213.

* cited by examiner

*Primary Examiner*—Johann Richter
*Assistant Examiner*—Brian J. Davis
(74) *Attorney, Agent, or Firm*—Charles F. Costello

(57) ABSTRACT

An improved process for the preparation of a 1,1,1-trifluoro-2-aminoalkane of formula I

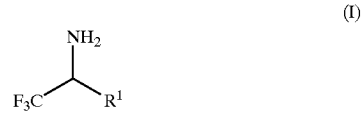

(I)

wherein $R^1$ represents an optionally substituted alkyl group;

which comprises hydrogenating the corresponding oxime of formula II

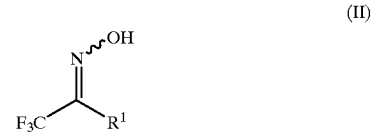

(II)

wherein $R^1$ has the meaning given above and the winding line indicates that the hydroxy group may be in the (E)- or (Z)-position with respect to the trifluoromethyl group, in the presence of Raney nickel and a diluent;

the improvement wherein is, that said reaction is carried out in a diluent selected from an alkanol, a cyclic ether and an aromatic hydrocarbon.

12 Claims, No Drawings

PROCESS FOR THE PREPARATION OF 1,1,1-TRIFLUORO-2-AMINOALKANES

This application claims priority from copending provisional application Ser. No. 60/129,472 filed on Apr. 15, 1999.

BACKGROUND OF THE INVENTION

The invention relates to an improved process for the preparation of 1,1,1-trifluoro-2-aminoalkanes which comprises hydrogenating the corresponding oximes.

1,1,1-trifluoro-2-aminoalkanes are useful as intermediates for the preparation of a variety of compounds which are useful as agrochemicals, pharmaceuticals or dyes. In particular, they are key intermediates in the preparation of insecticidal benzamides as disclosed for example by DE 36 11 193 and of fungicidal 7-(1,1,1-trifluoroalk-2-ylamino)-6-(halophenyl)-triazolopyrimidines which are described for example in PCT/US98/05615.

J. B. Dickey et al., Ind. Eng. Chem. 98, 1956, 209–213 disclose a method for the preparation of 1,1,1-trifluoro-2-aminopropane by the hydrogenation of the corresponding oxime in a rocking autoclave at a pressure of 150 bar (2.000 p.s.i.) in the presence of Raney Nickel using ether as diluent. However, only 30% of the desired product are obtainable according to this method.

Therefore, the method known from the art is not applicable for large scale production, due to its low yields.

SUMMARY OF THE INVENTION

Surprisingly, the 1,1,1-trifluoro-2-aminoalkanes of formula I

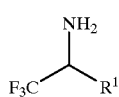

(I)

wherein
$R^1$ represents an optionally substituted alkyl group;
can be obtained in high yields by hydrogenation of corresponding oximes of formula II

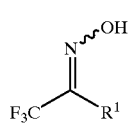

(II)

wherein $R^1$ has the meaning given above and the winding line indicates that the hydroxy group may be in the (E)- or (Z)-position with respect to the trifluoromethyl group, in the presence of Raney nickel and a diluent; when the reaction is carried out in a diluent selected from an alkanol, a cyclic ether or an aromatic hydrocarbon.

It is, therefore, an object of the present invention to provide an efficient improved process for the preparation of 1,1,1-trifluoro-2-aminoalkanes of formula I.

Other objects and advantages of the present invention will be apparent to those skilled in the art from the following description and the appended claims.

DETAILED DESCRIPTION OF THE PREFERRED EMBODIMENTS

The invention relates to an improved process for the preparation of the compounds of formula I by the hydrogenation of the oximes of formula II the improvement wherein is that the hyrogenation is carried out in a diluent selected from an alkanol, a cyclic ether or an aromatic hydrocarbon.

In general terms, unless otherwise stated herein, the term alkyl as used herein with respect to a radical or moiety refer to a straight or branched chain radical or moiety. As a rule, such radicals have up to 10, in particular up to 6 carbon atoms. Suitably an alkyl moiety has from 1 to 6 carbon atoms, preferably from 1 to 3 carbon atoms. A particularly preferred alkyl moiety is the methyl group.

Suitable alkanols are straight chained or branched alkanols with up to 6 carbon atoms, preferably 1 to 4 carbon atoms. Most preferred are methanol, ethanol and isopropanol, in particular methanol.

Suitable cyclic ethers are cyclic ethers having 4 to 6 carbon atoms and 1 or 2 non-adjacent oxygen atoms, in particular tetrahydrofuran and dioxane.

Suitable aromatic hydrocarbons are aromatic hydrocarbons having 6 to 9 carbon atoms, in particular benzene, toluene or xylene.

A preferred embodiment of the present invention is a process wherein:

1 part of the oxime of formula II is diluted with 5 to 15 parts, preferably 7.5 to 12.5 parts, in particular 8 to 10 parts of methanol, tetrahydrofuran or toluene;

Raney nickel is used in moist form, in particular moisturized with methanol, the mixture consisting of the oxime of formula II, the diluent and Raney nickel is kept under a hydrogen atmosphere at temperatures between 50° C. and 150° C., preferably between 75° C. and 120° C., in particular between 80° C. and 110° C.; most preferred at about 90° C.

the mixture consisting of the oxime of formula II, the diluent and Raney nickel is kept under a hydrogen atmosphere for 1 to 5 hours, preferably 2 to 4 hours, in particular about 3 hours;

the hydrogenation is carried out at a pressure of 25 to 100 bar, preferably 30 to 80 bar, in particular 35 to 70 bar most preferred at a pressure of about 50 bar;

the reaction mixture obtained form the hydrogenation is filtered and the resulting filtrate is acidified with a mineral acid, preferably hydrochloric acid, to obtain the corresponding 1,1,1-trifluoro-alk-2-yl ammonium salt;

the 1,1,1-trifluoro-alk-2-yl ammonium salt is separated and treated with a base, preferably with an alkali hydroxide, in particular sodium hydroxide to obtain the compound of formula I;

$R^1$ represents a $C_{1-4}$ alkyl group being optionally substituted by one or more halogen atoms or an alkoxycarbonyl or hydroxycarbonyl group, in particular wherein $R^1$ represents a methyl group.

The compound of formula II is preferably 1,1,1-trifluoropropanone oxime or ethyl 1,1,1-trifluoroacetylacetate oxime, which can be prepared by a condensation reaction between commercially available 1,1,1-trifluoropropanone or ethyl 1,1,1-trifluoroacetylacetate and hydroxylamine. This reaction is preferably carried out in the presence of a dehydration agent such as molecular sieves, $TiCl_4$ or sodium acetate as disclosed for example by J. B. Dickey et al., loc. cit.

The crude product obtained can be purified according to standard methods for example by distillation or chromatographic methods.

However, the crude product obtained according to the process of this invention is as a rule pure enough to be used as intermediate without further purification.

In a particularly preferred embodiment of the process according to this invention a mixture of the oxime of formula I (3 parts), the diluent, preferably methanol (25 to 35 parts) and Raney nickel (preferably moisturized with methanol; 1 to 1.5 parts) is hydrogenated in an autoclave at a pressure of about 50 bar and a temperature of about 90° C. until the hydrogen uptake ceases. The reaction mixture is cooled, filtered and treated with a mineral acid, in particular hydrochloric acid, and evaporated. The residue is treated with sodium hydroxide and the obtained amine of formula I is distilled.

In order to facilitate a further understanding of the invention, the following illustrative examples are presented. The invention is not limited to the specific embodiments described or illustrated, but encompasses the full scope of the appended claims.

EXAMPLE 1

Preparation of 1,1,1-trifluoropropanone oxime 3720 g of hydroxylamine hydrochloride were added to a solution of 5271 g of sodium acetate in 21 l water. Subsequently, 3000 g of 1,1,1-trifluoroacetone were dosed within 45 minutes at a temperature range of −5° C.–+8° C. The reaction mixture was stirred at room temperature for 3 days. After the stirrer has been switched off the phases separated. The crude oxime was diluted with a solution of sodium carbonate (700 g) in 5 l water. The oxime was separated and dried to yield 2912 g of the crude product which was used for the preparation of 2-amino-1,1,1-trifluoropropylamine without further purification.

EXAMPLE 2

Preparation of 2-amino-1,1,1-trifluoropropylamine hydrochloride

An autoclave was charged with 2986 g of 1,1,1-trifluoropropanone oxime obtained in Example 1, 1 kg of Raney nickel (moisturized with methanol) and 30 l of methanol. The autoclave was pressurized with 1400 l of hydrogen at a pressure of 50 bar and heated to 90° C. After a hydrogenation time of 2.5 h and a consumption of 64.5 bar the reaction mixture was cooled to room temperature and filtered. The filtrate was cooled down to 0° C. and acidified with concentrated hydrochloric acid. The acidified solution was evaporated to dryness and the precipitate washed with diethylether and dried to yield 2974.3 g (86%) of 2-amino-1,1,1-trifluoropropane hydrochloride having a melting point of 254–256° C.

EXAMPLE 3

Preparation of 2-amino-1,1,1-trifluoropropylamine 2974.3 g 2-amino-1,1,1-trifluoropropane hydrochloride obtained in Example 2 was placed in a three necked flask with stirrer, dropping funnel and descending condenser. The oil bath was heated up to 90° C. and an aqueous sodium hydroxide solution (40%) was added to the hydrochloride. The liberated amine distilled off and 2456.8 g (98%) of the product were collected having a boiling point of 46–47° C.

EXAMPLES 4 to 7

Preparation of 2-amino-1,1,1-trifluoropropylamine hydrochloride

An autoclave was charged with 12.7 g of the oxime obtained in Example 1.6 g of Raney nickel and 130 ml of the diluent indicated in Table I. The autoclave was pressurized with 6 l of hydrogen at the indicated pressure and heated to 90° C. After a hydrogenation time of 1.5 hours the reaction mixture was cooled to room temperature and filtered. The filtrate was cooled down to 0° C. and acidified with concentrated hydrochloric acid. The acidified solution was evaporated to dryness and the precipitate washed with diethylether and dried to obtain 2-amino-1,1,1-trifluoropropane hydrochloride with the yields shown in Table I.

TABLE I

| Example | diluent | pressure (bar) | Yield (%) |
|---|---|---|---|
| 4 | methanol | 50 | 73.5 |
| 5 | toluene | 50 | 60.2 |
| 6 | THF | 50 | 63.5 |
| 7 | ethanol | 50 | 78.0 |
| comparison | diethylether | 140 | 30.0 |

What is claimed is:

1. In a process for the preparation of a 1,1,1-trifluoro-2-aminoalkane of formula I

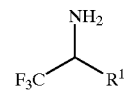

(I)

wherein

R$^1$ represents an optionally substituted alkyl group;
which comprises hydrogenating the corresponding oxime of formula II

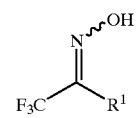

(II)

wherein R$^1$ has the meaning given above and the winding line indicates that the hydroxy group may be in the (E)- or (Z)-position with respect to the trifluoromethyl group, in the presence of Raney nickel in a diluent; wherein the improvement is, that the reaction is carried out in a diluent selected from an alkanol, a cyclic ether and an aromatic hydrocarbon and with the proviso that the 1,1,1-trifluoro-2-aminoalkane is obtained at a yield of greater than thirty percent.

2. A process according to claim 1, wherein the yield is at least about sixty percent.

3. A process according to claim 2, wherein 1 part of the oxime of formula II is diluted with 5 to 15 parts of methanol, tetrahydrofuran or toluene.

4. In a process for the preparation of a 1,1,1-trifluoro-2-aminoalkane of formula I

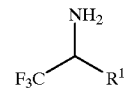

(I)

wherein

R$^1$ represents an optionally substituted alkyl group;

which comprises hydrogenating the corresponding oxime of formula II

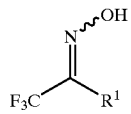
(II)

wherein $R^1$ has the meaning given above and the winding line indicates that the hydroxy group may be in the (E)- or (Z)-position with respect to the trifluoromethyl group, in the presence of Raney nickel in moist form and a diluent;

wherein the improvement is, that the reaction is carried out in a diluent selected from an alkanol, a cyclic ether and an aromatic hydrocarbon.

5. A process according to claim 4, wherein Raney nickel is moisturized with methanol.

6. In a process for the preparation of a 1,1,1-trifluoro-2-aminoalkane of formula I

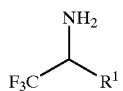
(I)

wherein $R^1$ represents an optionally substituted alkyl group;

which comprises hydrogenating the corresponding oxime of formula II

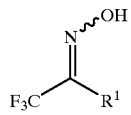
(II)

wherein $R^1$ has the meaning given above and the winding line indicates that the hydroxy group may be in the (E)- or (Z)-position with respect to the trifluoromethyl group, in the presence of Raney nickel and a diluent;

wherein the improvement is, that the reaction is carried out in a diluent selected from an alkanol, a cyclic ether and an aromatic hydrocarbon, and the mixture consisting of the oxime of formula II, the diluent and Raney nickel is kept under a hydrogen atmosphere at temperatures between 50° C. and 150° C.

7. A process according to claim 6, wherein the mixture consisting of the oxime of formula II, the diluent and Raney nickel is kept under a hydrogen atmosphere for 1 to 5 hours.

8. A process according to claim 4, wherein the hydrogenation is carried out at a pressure of 25 to 100 bar.

9. A process according to claim 8, wherein the reaction mixture obtained from the hydrogenation is filtered and the resulting filtrate is acidified with a mineral acid to obtain the corresponding 1,1,1-trifluoro-alk-2-yl ammonium salt.

10. A process according to claim 9, wherein the 1,1,1-trifluoro-alk-2-yl ammonium salt is separated and treated with a base to obtain the compound of formula I.

11. In a process for the preparation of a 1,1,1-trifluoro-2-aminoalkane of formula I

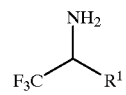
(I)

wherein $R^1$ represents a $C_{1-4}$ alkyl group optionally substituted by one or more halogen atoms or an alkoxycarbonyl group;

which comprises hydrogenating the corresponding oxime of formula II

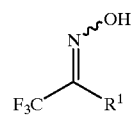
(II)

wherein $R^1$ has the meaning given above and the winding line indicates that the hydroxy group may be in the (E)- or (Z)-position with respect to the trifluoromethyl group, in the presence of Raney nickel and a diluent;

wherein the improvement is, that the reaction is carried out in a diluent selected from an alkanol, a cyclic ether and an aromatic hydrocarbon.

12. A process according to claim 11, wherein $R^1$ represents a methyl group.

* * * * *